United States Patent [19]

Stone et al.

[11] 4,226,944
[45] Oct. 7, 1980

[54] PROCESS FOR A POLYURETHANE FOAM CONTAINING FRAGRANCE

[75] Inventors: Herman Stone, Hazleton; Peter D. Pauly, Mountaintop, both of Pa.

[73] Assignee: Tenneco Chemicals, Inc., Saddle Brook, N.J.

[21] Appl. No.: 960,390

[22] Filed: Nov. 13, 1978

[51] Int. Cl.² ............... C08G 18/14; C08G 18/08; A61L 9/01

[52] U.S. Cl. ............... 521/76; 252/522 R; 252/522 A; 239/53; 239/54; 239/60; 424/19; 424/78; 521/121; 521/122; 521/125; 521/160; 521/905

[58] Field of Search ............... 252/522 R, 522 A; 521/76, 122, 121, 125, 905, 160; 239/54, 53, 60; 424/19, 78

[56] References Cited

U.S. PATENT DOCUMENTS

| | | | |
|---|---|---|---|
| 3,029,209 | 4/1962 | Ferrigno | 521/76 |
| 3,080,256 | 3/1963 | Bundy | 260/29.3 X |
| 3,151,993 | 10/1964 | Bundy | 106/20 |
| 3,476,845 | 11/1969 | Buff et al. | 264/54 |
| 3,544,364 | 12/1970 | Rudner et al. | 428/452 X |
| 3,608,062 | 9/1971 | Alfes et al. | 239/60 |
| 3,630,446 | 12/1971 | Roth et al. | 239/60 |
| 3,688,985 | 9/1972 | Engel | 252/522 A |
| 3,810,841 | 5/1974 | Richter | 521/125 |
| 4,051,159 | 9/1977 | Boucalas et al. | 260/18 N |
| 4,124,518 | 11/1978 | Stone et al. | 521/905 |
| 4,129,694 | 12/1978 | Cogliano et al. | 521/125 |

Primary Examiner—H. S. Cockeram
Attorney, Agent, or Firm—James P. Scullin

[57] ABSTRACT

Fragrance-emitting articles comprising a polyurethane foam containing a particulate filler and a fragrance material, and a method of making such articles, are disclosed. The method includes the essential steps of pre-mixing particulate filler and fragrance and dispersing the pre-mix in a liquid polyol, before adding the other reaction mixture components, and provides a polyurethane foam having a controlled rate of release of the fragrance.

26 Claims, No Drawings

PROCESS FOR A POLYURETHANE FOAM CONTAINING FRAGRANCE

FIELD OF THE INVENTION

This invention pertains to polyurethane foam containing a fragrance, and to a method of making same. The fragrance is released at a controlled rate, making the polyurethane articles suitable for use as pomanders, garment sachets, room air-fresheners, and the like.

BACKGROUND OF THE INVENTION

Various compositions and devices meant to release a fragrance over a long period of time are well known. The fragrances employed include both aromatic and perfumed compositions. An early form of such a device, and one still in use, was a pomander made by studding an apple or orange with cloves, used as a garment sachet. Another approach still in use is to enclose dried leaves or flower petals in a perforated bag, box, or other container. More recently, various solid substrates such as waxes or polymeric materials have been impregnated with fragrances and used, for example, as room air-fresheners. In such applications, a steady and controlled rate of release of the fragrance from the substrate is a desirable attribute. The use of waxes or polymeric materials as substrates or carriers has the further advantage that the fragrance-containing material can readily be formed or cut into virtually any desired shape or size.

As specific examples of prior art materials, U.S. Pat. No. 2,169,055 discloses sheets of plasticized cellulose acetate containing essential oils; U.S. Pat. No. 3,655,129 discloses a polymeric substrate in which is dispersed droplets of a liquid non-solvent containing fragrance oil; and U.S. Pat. No. 4,051,159 discloses a transparent article comprising a mixture of a polyamide resin, a long-chain alkyl alcohol, and a fragrance material. A somewhat different, but related, approach is that disclosed in U.S. Pat. No. 3,544,364 naming Rudner et al as inventors. In this case a solid hydroxylated substrate such as paper or cotton is treated with a prolonged odor releasing composition.

Each of the prior art compositions has some disadvantage such as high cost, inadequate rate of release of the fragrance, difficulty in forming and maintaining a desired shape, and so on. These disadvantages have led to a continuing search for improvements in odor-releasing compositions.

We have found that the disadvantages or prior compositions can be overcome, and that improvements can be obtained, by the use of certain polyurethane foam compositions as carriers for fragrances, in the manner described herein.

SUMMARY OF THE INVENTION

The present invention provides fragrance emitting polyurethane foam compositions, made by the inclusion of fragrances in foam-forming reaction mixtures. These polyurethane foam compositions can be flexible, semi-flexible, or rigid, but flexible foams are preferred.

The foams are characterized by a steady and controlled rate of release of the fragrance contained therein, can be obtained in any desired size and shape, and can be produced by either batch or continuous processes. They are low in cost, light in weight, practically unbreakable, can be made in any color desired, and are eminently suitable for use as air-fresheners, garment sachets, and the like.

Briefly, the foams of this invention are prepared by premixing the fragrance material with a dry particulate filler, adding this premix to a liquid polyol to form a second mixture, and then introducing the second mixture into a reaction zone together with an organic di-or polyisocyanate, a blowing agent, and a catalyst, to produce a polyurethane foam-forming reaction mixture. A similar process, with the exception that no fragrance is used, is described in our pending and commonly-assigned patent application Ser. No. 780,701, filed on Mar. 24, 1977. The dry particulate filler can be, illustratively, clay, limestone, soap, detergent, or mixtures thereof. Those skilled in the art will understand that other materials conventionally used in the manufacture of polyurethane foams (for example, surfactants, colorants, and flame-retardants) can also be included in the reaction mixture.

The fragrance-containing foams of this invention can be made by any of the methods known in the art, and either batchwise or continuously, and in any desired size or shape. Continuous processes are preferred, in which the foam is made in the form of buns having either a substantially circular cross-section using, for example, the method of Buff et al. in U.S. Pat. No. 3,476,845, or a substantially rectangular cross-section. Such buns can then be cut into any convenient length, and peeled or split into sheets of any desired thickness using any method and apparatus known in the art.

DETAILED DESCRIPTION OF THE INVENTION

The liquid polyols, organic di-or polyisocyanates, blowing agents, and catalysts which can be used in the practice of this invention are those used in the art to make conventional polyurethane foams.

The normally liquid polyols suitable for use in preparing the polyurethane foam can be polyether polyols, polyester polyols, or mixtures of at least one polyether polyol and at least one polyester polyol, although polyether polyols are preferred. Also, a single polyether polyol or polyester polyol can be used, as well as mixtures of two or more polyether polyols or two or more polyester polyols. In addition, minor quantities of low molecular weight diols can be present in the reaction.

The normally liquid polyether polyol used in the practice of this invention can be one which is conventionally used in the art in the manufacture of flexible polyurethane foams. The polyol is usually a derivative of 1,2-propylene oxide or both 1,2- propylene oxide and ethylene oxide, the ethylene oxide amounting to up to about 30 percent by weight of the propylene oxide and ethylene oxide. When ethylene oxide is used, the ethylene oxide residues can be present at blocks or can be alternately or randomly distributed. In the manufacture of the polyol, the propylene oxide or both propylene oxide and ethylene oxide are reacted with a polyhydric initiator, such as glycerol, trimethylol ethane, trimethylolpropane, or 1,2,6-hexanetriol. Some representative polyether polyols which are useful in practicing this invention are: Voranol 3140 or CP-3140 manufactured by Dow Chemical; PG-412 manufactured by Olin; F-3514 manufactured by Jefferson Chemical; and E-363 manufactured by Union Carbide. In general, the normally liquid polyether polyol used will have an average molecular weight within the range from about 2000 to about 7000 and a hydroxyl number within the range from about 25 to about 150.

The polyester polyol reactants useful in preparing the polyurethane foam include any conventionally used in the preparation of urethane polymer foams. The polyhydric polyester reactant usually has a molecular weight of a least about 400 and optimally between about 500 and about 5000. The hydroxyl number of the compound is correspondingly in the range of from about 15 to about 300. The preferred average hydroxyl functionality for the polyester resins is from about 2.2 to 2.8.

The range of polyester polyol compounds useful for preparing the polyurethane foams in the present invention is well known to the art, and the polyester polyol compounds can be prepared by, for example, the reaction of a polyhydric alcohol with a polycarboxylic acid compound, each containing from two to about 36 or more carbon atoms in the molecule. The polycarboxylic acid includes such acid precursors as the corresponding acid anhydrides or acid halides or even, for example, alkyl esters. The preferred acids are the di-carboxylic acids containing from 4 to 36 carbon atoms in the molecule. Examples of such preferred carboxylic acid compounds which can be used include, for example, aromatic acids, such as phthalic acid, terephthalic acid, isophthalic acid, tetrachlorophthalic acid, cycloaliphatic acids such as cyclohexane-1,4-diacetic acid, but especially the aliphatic acids such as tricarballylic, oxydipropionic, succinic, glutaric, adipic, azelaic, suberic and sebacic acids, hydrogenated fatty acid dimer, or combinations of such acids. The polyester polyols can also be prepared from the corresponding lactones, such as gamma-butyrolactone or epsilon-caprolactone, for example.

The polyhydric alcohol used in the preparation of the polyester polyol is generally a mixture of a dihydric and a trihydric alcohol. Preferably, a mixture of polyols, the major portion having a functionality of two and the minor a functionality of three, is used. This mixture of di- and tri-functional polyols is utilized to give an average functionality of between about 2.2 and 2.8. A functionality of greater than two is desirable to provide cross-linking in the reaction between the polyester polyol and the polyisocyanate.

It is recognized that certain compounds which are considered by those skilled in the art as polyester resins also contain ether linkages, e.g., esters prepared from dipropylene glycol. However, the primary character of such resins is considered to be that of an ester.

In addition to the normally liquid polyether or polyester polyol, the reaction mixture from which the foam is produced can also contain a diol having from 2 to 8 carbon atoms, inasmuch as the use of such a diol increases the tensile and tear strengths of the foam, particularly when wet. Among the useful diols are ethylene glycol, diethylene glycol, triethylene glycol, propylene glycol, dipropylene glycol, trimethylene glycol, 1,2-butanediol, 1,3-butanediol and 1,4-cyclohexane dimethanol. In general, the amount of diol used will be within the range from about two to about ten percent by weight, based upon the weight of the normally liquid polyol.

The organic polyisocyanates useful in the preparation of the polyurethane foam are also conventional. They contain at least two isocyanate groups per molecule. Preferably, the isocyanate mixture selected has an isocyanate functionality of from 2.0 to 3.0. The most useful isocyanates are the aromatic polyisocyanates, alone or admixed with aliphatic, cycloaliphatic or heterocyclic polyisocyanates.

The aromatic diisocyanates are generally the least expensive and most reactive polyisocyanates available. The aromatic diisocyanates, especially the toluene diisocyanate isomers, are used commercially in the preparation of foam by the one-shot, continuous slab-stock process. However, for certain purposes, other polyisocyanates, especially the aliphatic, aralkyl and cycloalkyl polyisocyanates have valuable properties and can be used, if desired, in admixture with, e.g., toluene diisocyanates. The aralkyl, aliphatic and cycloaliphatic polyisocyanates are especially useful when resistance against degradation and discoloration due to oxidation or light is needed. The non-aryl polyisocyanates are generally not useful alone, but can be used in combination with the other types for special purposes.

Suitable organic polyisocyanates include, for example, n-butylene diisocyanate, methylene diisocyanate, m-xylene diisocyanate, p-xylene diisocyanate, cyclohexyl-1, 4-diisocyanate, dicyclohexylmethane-4, 4'-diisocyanate, m-phenylene diisocyanate, p-phenylene diisocyanate, 3-(alphaisocyanatoethyl)-phenyl isocyanate, 2,6-diethylbenzene-1,4-diisocyanate, diphenyldimethylmethane-4, 4'-diisocyanate, ethylidene diisocyanate, propylene-1 2-diisocyanate, cyclohexylene-1, 2-diisocyanate, 2,4-tolylene diisocyanate, 2,6-tolylene diisocyanate, 3,3'-dimethyl-4'-biphenylene diisocyanate, 3,3'-dimethoxyl-4,4'-biphenylene diisocyanate, 3,3-diphenyl-4,4'-biphenylene diisocyanate, 4,4'-biphenylene diisocyanate, 3,3'-dichloro-4,4'-biphenylene diisocyanate, 1,5-naphthylene diisocyanate, isophorone diisocyanate, m-xylylene diisocyanate, triazine tri-isocyanate, triketotrihydrotris (isocyanatophenyl) triazine and tris (isocyanatophenyl) methane.

Generally, in carrying out the urethane polymerization reactions, the only significant groups in the reactant compounds are the isocyanate groups and active hydrogen groups which are reactive therewith. Acyclic, alicyclic, aromatic and heterocyclic radicals are all possible substituents on the active hydrogen and polyisocyanate reactants.

Tolylene diisocyanate is preferred for reaction with the normally liquid polyol and the diol, if used, to form the polyurethane and also for reaction with the water introduced into the reaction mixture to form carbon dioxide which expands the polyurethane. Most preferably, the tolylene diisocyanate used is the 65 percent, 2,4-isomer, 35 percent 2,6-isomer mixture (TDI 65/35), but other tolylene diisocyanates, such as the 2,4-isomer in pure form; the 80 percent 2,4-isomer, 20 percent 2,6-isomer mixture (TDI 80/20); or a 2,4-isomer, 2,6-isomer mixture containing at least 65 percent of the 2,4-isomer can also be used. Those skilled in the art will readily understand how much tolylene diisocyanate and water to introduce into the reaction mixture, and in this connection the accompanying Examples serve as a guide.

Particulate or pulverulent fillers which are useful in the practice of this invention include, but are not limited to, clays including both untreated clays and those which have been surface treated in various ways well known in the art, ground limestone, precipitated calcium carbonate including surface treated types, alumina, aluminum silicate, barytes, wollastonite or other calcium silicate, silica, zirconia, titanium dioxide, soap, and synthetic detergents in solid form.

The synthetic detergent can be, for example, an alkylaryl sulfonate detergent, such as a sodium alkyl benzene sulfonate or sodium alkyl naphthalene sulfonate. Where the sulfonate used is an alkyl benzene sulfonate, the benzene ring of the sulfonate will usually have only one alkyl substituent and such substituent will contain from 8 to 18 carbon atoms. Among such alkyl benzene sulfonates are sodium linear dodecylbenzene sulfonate, sodium keryl benzene sulfonate, sodium tridecylbenzene sulfonate and sodium nonylbenzene sulfonate. On the other hand, where the sulfonate used is an alkyl naphthalene sulfonate, the naphthalene ring of the sulfonate will usually have one or two alkyl substituents and the total number of carbon atoms in the alkyl substituents will be between 3 and 10. Among such sulfonates are sodium monoisopropylnaphthalene sulfonate, sodium diisopropylnaphthalene sulfonate, sodium diamylnaphthalene sulfonate and sodium monocaprylnaphthalene sulfonate. The sulfonates in solid form are commercially available in 40 to 90 percent by weight active form, the rest being predominantly sodium sulfate. In practicing the present invention, it is preferred to use the 90 percent active form, which is the highest available commercially, but other forms can also be used. When the sulfonate is marketed admixed with water, the water serves to generate carbon dioxide for foam forming by reaction with the isocyanates.

Useful clay fillers are described in U.S. Pat. No. 3,080,256, patented Mar. 5, 1963, naming Wayne M. Bundy as the inventor. As is disclosed in the Bundy patent, such compositions can be prepared by a procedure involving coating kaolin with a small amount (for example, from about 0.2 percent to about 2 percent by weight, based on the weight of the kaolin) of a polyamine, such as ethylene diamine, hexamethylene diamine, tetraethylene diamine, diethylene triamine, tetraethylene pentamine and guanidine.

Other useful clay fillers are described in U.S. Pat. No. 3,151,993, patented Oct. 6, 1964, also naming Wayne M. Bundy as the inventor. As is disclosed in this patent, such fillers can be prepared by a procedure involving coating kaolinite particles with aluminum hydroxide precipitated in situ at a pH between about 7.5 to 9. We prefer to use clay, limestone, soap, linear dodecylbenzene sodium sulfate, combinations of clay and linear dodecylbenzene sodium sulfonate, or combinations of clay and soap. Other particulate or pulverulent fillers can also be used, including those used in the preparation of conventional urethane foams. The only limitations are that the fillers do not adversely affect the urethane foam-forming reaction, and do not react with the fragrance to be used nor absorb the fragrance to such a degree that release from the finished foam is unduly inhibited or entirely prevented. The particle size of the filler is not critical, and can be varied over a wide range, although very coarse particles are generally undesirable because they may detract from the esthetic properties of the finished foam. We prefer to use fillers having a particle size of 50 microns or less in the largest dimension although larger particle sizes can be used if desired without departing from the scope of the invention.

The amount of filler can be varied over a wide range, depending on the amount of fragrance to be added and the viscosity of the blend of fragrance, filler and liquid polyol. The blend should be sufficiently low in viscosity to be handled as a liquid. We have found that filler levels of between about 5 and about 100 parts by weight per 100 parts by weight of polyol are generally satisfactory, although greater or lesser amounts can be used if desired.

Any type of fragrance can be used in the practice of this invention, provided that it does not react with organic di-or polyisocyanates and that it is heat stable at the temperatures generated in the formation of polyurethane foams. Fragrances are usually complex mixtures. We prefer to use fragrances containing esters, terpenes, aldehydes, and/or ketones. Those which contain functional groups reactive with organic polyisocyanates and which lost their odor after reaction, and those which are very low-boiling or heat-sensitive and would thus be lost or destroyed during the exothermic foaming reaction, are generally unsuitable. The amount of fragrance is not critical, and can be varied over a wide range, depending on such factors as the intensity of the odor desired for a given application and the desired useful life of the fragrance-emitting foam composition. Generally, it will be desired to incorporate a high level of fragrance in order to obtain a long useful life. By way of illustration, we have found that fragrance levels of from about 0.25 parts by weight to about 20 parts by weight per 100 parts by weight of polyol in the foam-forming reaction mixture, are usable although lesser or greater levels can be used if desired. We prefer to use from about 1 part by weight to about 5 parts by weight per 100 parts by weight of polyol.

The examples which follow include examples illustrative of the invention, but not limitative thereof, as well as comparative examples.

EXAMPLE 1

An intimate mixture was prepared by blending together 35 parts by weight of Kaogen 7 (a proprietary clay having a median particle diameter of about 0.77 microns, produced by Georgia Kaolin Co.), 60 parts by weight of linear dodecylbenzene sodium sulfonate, and 6 parts by weight of a fragrance (Herbal 776867, produced by Bush Boake Allen Inc.). This first mixture was then uniformly dispersed in 100 parts by weight of a liquid polyether polyol (CP-3140 produced by Dow Chemical Co.) having a molecular weight about 3800 and a hydroxyl number of about 45 to form a second mixture. The second mixture was then intimately blended with 38.4 parts by weight of tolylene diisocyanate (65/35 ratio of 2,4-isomer/2,6-isomer), 0.5 parts by weight of water, 5.0 parts by weight of 1,4-cyclohexane dimethanol (CHDM), 1,8 parts by weight of a 33% solution of triethylene diamine in dipropylene glycol (33LV), 0.35 parts by weight of stannous octoate, 0.1 parts by weight of L-6202 (a silicone surfactant produced by Union Carbide Corp.), and 5.0 parts by weight of a green pigment dispersion. This reaction mixture, having a TDI index of 123, had a cream time of 6 seconds and a rise time of 210 seconds. The resulting foam was strong, flexible and resilient, with uniform cell structure. The foam, after being cooled to room temperature, and cut into $3 \times 2\frac{1}{2} \times \frac{3}{8}$ inch pieces, emitted a pleasant herbal odor, and continued to do so for at least three months, at ambient conditions.

EXAMPLE 2

Example 2 is a comparator which contained no fragrance, but was otherwise identical in composition to Example 1. The reaction mixture had a cream time of 6 seconds and a rise time of 200 seconds. The resulting foam was strong, flexible and resilient with uniform cell structure.

With the exception of the odor emitted from the product of Example 1, the foams of both examples were essentially identical, showing that the fragrance added to the reaction mixture had no adverse effect on the foam-forming reaction.

EXAMPLE 3

Example 1 was repeated, except that 6 parts by weight of a citrus fragrance (Citrus 777050 produced by Bush Boake Allen, Inc.) was used in place of the herbal fragrance. The results were essentially the same, the pieces of foam yielding a sustained release of citrus aroma for a long period of time.

EXAMPLE 4

Example 1 was repeated, except that the order of addition of the ingredients was changed. In this comparative example which is not illustrative of the invention, a first mixture was prepared by blending the herbal fragrance with the polyether polyol, then adding the dodecylbenzene sodium sulfonate followed by the clay to form a second mixture. The second mixture was then blended with the other foam-forming reactants as in Example 1. The foam was identical in appearance and properties to that of Example 1, and was cut into $3 \times 2\frac{1}{2} \times \frac{5}{8}$ pieces. The foam pieces initially emitted a pleasant herbal odor, but it quickly dissipated. Fresh surfaces were exposed by cutting off a portion of the foam piece, and the herbal odor was again emitted but quickly dissipated as before. This example shows the importance of the proper order of addition in forming the first and second mixtures.

EXAMPLES 5-8

These are comparative examples showing the effect of adding fragrances to conventional polyurethane foam-forming reaction mixtures which do not contain dry particulate fillers.

In Example 5, a foam was prepared by mixing together 100 parts by weight of GP3000-1 (a 3000 molecular weight polyether polyol produced by Choate Chemical Co.), 1.25 parts by weight L6202 (silicone surfactant), 4.5 parts by weight water, 0.1 parts by weight NIAX A-1 (70% solution of bis (2-dimethylaminoethyl) ether in dipropylene glycol, sold by Union Carbide Corp.), 0.033 parts by weight of a 33% solution of triethylene diamine in dipropylene glycol, 0.27 parts by weight of stannous octoate, and 56.35 parts by weight of tolylene diisocyanate (80/20 mixture of 2,4-isomer/2,6-isomer). This mixture, which had an index of 108, had a cream time of 12 seconds and a rise time of 75 seconds, formed a strong, resilient foam of uniform cell structure and a density of 1.56 lb/cu.ft.

Examples 6, 7, and 8 are replicates of Example 6, except that the stannous octoate level was increased to 0.35 parts by weight and 2.5 parts by weight of a fragrance was added. In example 6 the fragrance was Herbal 777049, in Example 7 it was Citrus 777050, and in Example 8 it was Ivory 777051 (all produced by Bush Boake Allen, Inc.). Each of these three examples had an index of 108. In Example 6 the cream time was 12 seconds and the rise time 80 seconds; in Example 7 the values were 13 seconds and 115 seconds; and in Example 8 the values were 9 seconds and 70 seconds. The densities of the resulting foams, which closely resembled that of Example 5 in appearance and properties, were 1.68 lb.cu.ft. for Example 6, 1.41 lb./cu.ft. for Example 7, and 1.58 lb./cu.ft. for Example 8.

When freshly prepared, each of Examples 6, 7 and 8 emitted pleasant odors, but in less than two weeks at room temperature little or no odor could be detected. Fresh surfaces were exposed by cutting each of the foam pieces, and the odors were again emitted initially, but again quickly dissipated. These examples show that in the absence of dry, particulate fillers used to form first mixtures with the fragrance in the manner disclosed herein, fragrances in conventional polyurethane foams become trapped in the interior of the foam structure and are emitted only from freshly exposed surfaces.

EXAMPLE 9

This is an example according to the invention, illustrating the use of limestone as the particulate filler. A first mixture was prepared by intimately blending together 100 parts by weight of ground limestone having an average particle size of about 50 microns and 5 parts by weight of a fragrance (Herbal 777510 produced by Bush Boake Allen, Inc.). The first mixture was then blended with 100 parts by weight of CP-3140 (a 3800 molecular weight polyether polyol from Dow Chemical Corp.) to form a second mixture. The second mixture was then intimately blended with 31.6 parts of tolylene diisocyanate (75/25 ratio of 2,4-isomer/2,6-isomer), 2.3 parts by weight of water, 2.0 parts by weight of L-6202, 0.23 parts by weight of NIAX A-1, 0.13 parts by weight of a 33% solution of triethylene diamine in dipropylene glycol, and 1.0 part by weight of stannous octoate. This reaction mixture, which had an index of 105, had a cream time of 5 seconds and a rise time of 120 seconds. The resulting foam, which had a uniform cell structure, had a density of 3.87 lb./cu.ft. It emitted a pleasing herbal scent for a protracted period of time, at least three months, at ambient conditions.

EXAMPLE 10

This is another example according to the invention, illustrating the use of clay as the particulate filter. A first mixture was prepared by intimately blending 30 parts by weight of clay (Kaogen 7) and 5 parts by weight of a fragrance (Herbal 777510). The first mixture was then blended with 100 parts by weight of CP-3140, to form a second mixture. The second mixture was then intimately blended with 25.2 parts of tolylene diisocyanate (75/25 ratio of 2,4-isomer/2,6-isomer), 1.7 parts by weight of water, 2.0 parts by weight of L-6202, 0.1 parts by weight of A-1, 0.13 parts by weight of a 33% by weight solution of triethylene diamine in diethylene glycol, and 1.0 part by weight of stannous octoate. This reaction mixture, which had an index of 105, had a cream time of 8 seconds and a rise time of 200 seconds. The resulting foam had uniform cell structure and a density of 4.36 lb./cu.ft. It emitted a pleasant herbal scent for at least three months, at ambient conditions.

EXAMPLES 11-14

Examples 11, 13 and 14 are additional examples made according to the invention, while Example 12 is a comparator which does not contain a fragrance. Example 11 is another example using linear dodecylbenzene sodium sulfonate (Ultrawet K, sold by Arco Chemical Corp.) and clay as the filler. In Examples 12 and 13 the filler was clay and soap, and in Example 14 the filler was soap. The soap used was a coco tallow soap, which was first dried to a moisture content of 0.07%. The fragrance used was Oriental 777505 made by Bush Boake Allen, Inc. Each of these examples had an index of 120.

The reaction mixtures had the following compositions, in parts by weight:

| Example No. | 11 | 12 | 13 | 14 |
|---|---|---|---|---|
| CP - 3140 | 100 | 100 | 100 | 100 |
| soap | — | 30 | 30 | 30 |
| Ultrawet K | 60 | — | — | — |
| Kaogen 7 | 35 | 15 | 15 | — |
| CHDM | 5.0 | — | — | — |
| water | 1.0 | 1.7 | 1.7 | 1.7 |
| L - 6202 | 0.2 | 0.067 | 0.067 | 0.067 |
| Dabco 33LV | 1.8 | 0.68 | 0.68 | 0.68 |
| red pigment | 1.0 | 1.0 | 1.0 | 1.0 |
| stannous octoate | 1.0 | — | — | — |
| tolylene diisocyanate (65/35) | 33.1 | 29.1 | 29.1 | 29.1 |
| fragrance | 6.2 | — | 6.2 | 6.2 |

In preparing these foams, first mixtures were formed by blending Ultrawet K, Kaogen 7 and fragrance (Example 11), soap and Kaogen 7 (Example 12), soap, Kaogen 7, and fragrance (Example 13), or soap and fragrance (Example 14). In each example, a second mixture was then formed by dispersing the first mixture into the polyol, CP-3140. The second mixture was then intimately blended with the other components, as in the case of previous examples.

The following rise and cream times were measured during the foam-forming reactions, and densities were determined on the resulting foams:

|  | 11 | 12 | 13 | 14 |
|---|---|---|---|---|
| cream time seconds | 12 | 9 | 10 | 11 |
| rise time seconds | 480 | 200 | 265 | 280 |
| density, lb./cu.ft. | 5.08 | 4.38 | 4.02 | 3.87 |

Examples 12, 13, and 14 were slightly tight, but were easily crushed to form open-celled, flexible, resilient foams. The foams containing fragrance, Examples 11, 13, and 14, emitted a pleasant aroma for at least three months, at ambient conditions.

EXAMPLES 15-18

These examples illustrate the use of a polyester polyol in the foam-forming reaction mixture, rather than a polyether polyol. The polyester was prepared from adipic acid, diethylene glycol, and a minor amount of trimethylolethane and had a molecular weight of approximately 2700 and a hydroxyl number of 56. Example 15 is a comparator, and Examples 16, 17, and 18 are made according to the invention using as the fragrance Oriental 777509 made by Bush Boake Allen, Inc. Each of these examples had an index of 103. The reaction mixtures had the following compositions, in parts by weight:

| Example No. | 15 | 16 | 17 | 18 |
|---|---|---|---|---|
| polyester polyol | 100 | 100 | 100 | 100 |
| water | 3.6 | 3.6 | 3.6 | 3.6 |
| silicone surfactant | 1.2 | 1.2 | 1.2 | 1.2 |
| NIAX ESN (3-dimethylamino proprionitrile) | 1.0 | 1.0 | 1.0 | 1.0 |
| N-hexadecyldimethylamine | 0.3 | 0.3 | 0.3 | 0.3 |
| orange pigment | 1.5 | 1.5 | 1.5 | 1.5 |
| Kaogen 7 | — | 10 | 10 | 10 |
| stannous octoate/Kronitex 100(FMC Corp.), 1/1 | 0.05 | 0.05 | 0.1 | 0.2 |
| fragrance | — | 1.0 | 1.0 | 1.0 |
| tolylene diisocyanante (80/20) | 44.1 | 44.1 | 44.1 | 44.1 |

In preparing Examples 16-18, first mixtures were made by blending clay and fragrance, second mixtures were then made by dispersing the first mixture into the polyester polyol, and the second mixtures were then intimately blended with the balance of the ingredients.

The following rise and cream times were measured uring the foam-forming reactions, and densities were measured on the resulting foams:

|  | 15 | 16 | 17 | 18 |
|---|---|---|---|---|
| cream time, seconds | 8 | 9 | 8 | 8 |
| rise time, seconds | 90 | 120 | 110 | 90 |
| density, lb./cu.ft. | 2.24 | 2.70 | 2.58 | 2.26 |

All of the foams were flexible and resilient. The foams from Examples 16-18 emitted a pleasing scent for an extended period of time, at least three months at ambient conditions.

What is claimed is:

1. A process for the manufacture of a polyurethane foam containing a particulate filler and a fragrance which comprises the steps of mixing at least one particulate filler with at least one fragrance material to form a first mixture, mixing said first mixture with at least one liquid polyol to form a second mixture, and then mixing said second mixture with at least one organic polyisocyanate, water, and at least one catalyst whereby a polyurethane foam capable of releasing fragrance at a controlled and steady rate is produced.

2. The process of claim 1 wherein the particulate filler is clay.

3. The process of claim 2 wherein the clay is kaolin coated with from about 0.2 to about 2 percent by weight, based upon the weight of the kaolin, of a polyamine.

4. The process of claim 3 wherein the polyamine is ethylene diamine.

5. The process of claim 1 wherein the particulate filler is limestone.

6. The process of claim 1 wherein the particulate filler is a combination of clay and soap.

7. The process of claim 1 wherein the particulate filler is a combination of clay and a synthetic detergent.

8. The process of claim 7 wherein the synthetic detergent is linear dodecylbenzene sodium sulfonate.

9. The process of claim 1 wherein the particulate filler is soap.

10. The process of claim 1 wherein the polyol is a polyether polyol.

11. The process of claim 1 wherein the polyol is a polyester polyol.

12. The process of claim 1 wherein the organic polyisocyanate is a 65/35 percent mixture of 2,4-tolylene diisocyanate/2,6-tolylene diisocyanate.

13. The process of claim 1 wherein the organic polyisocyanate is a 75/25 percent mixture of 2,4-tolylene diisocyanate/2,6-tolylene diisocyanate.

14. The product of the process of claim 1.
15. The product of the process of claim 2.
16. The product of the process of claim 3.
17. The product of the process of claim 4.
18. The product of the process of claim 5.
19. The product of the process of claim 6.
20. The product of the process of claim 7.
21. The product of the process of claim 8.
22. The product of the process of claim 9.
23. The product of the process of claim 10.
24. The product of the process of claim 11.
25. The product of the process of claim 12.
26. The product of the process of claim 13.

* * * * *